(12) United States Patent
Aggarwal

(10) Patent No.: US 7,241,576 B2
(45) Date of Patent: Jul. 10, 2007

(54) USES OF THANK, A TNF HOMOLOGUE THAT ACTIVATES APOPTOSIS

(75) Inventor: Bharat B. Aggarwal, Houston, TX (US)

(73) Assignee: Research Development Foundation, Carson City, NV (US)

( * ) Notice: Subject to any disclaimer, the term of this patent is extended or adjusted under 35 U.S.C. 154(b) by 702 days.

(21) Appl. No.: 10/170,812

(22) Filed: Jun. 13, 2002

(65) Prior Publication Data

US 2003/0166546 A1    Sep. 4, 2003

Related U.S. Application Data

(62) Division of application No. 09/496,118, filed on Feb. 1, 2000, now Pat. No. 6,475,986.

(60) Provisional application No. 60/118,531, filed on Feb. 2, 1999, now abandoned.

(51) Int. Cl.
| | |
|---|---|
| G01N 33/53 | (2006.01) |
| G01N 33/567 | (2006.01) |
| G01N 33/574 | (2006.01) |
| C12Q 1/00 | (2006.01) |
| A61K 38/00 | (2006.01) |
| C07K 14/00 | (2006.01) |
| C07K 16/00 | (2006.01) |
| C07K 17/00 | (2006.01) |
| C07K 2/00 | (2006.01) |
| C07K 4/00 | (2006.01) |
| C07K 5/00 | (2006.01) |

(52) U.S. Cl. ............... 435/7.1; 435/4; 435/7.21; 435/7.23; 436/57; 436/86; 436/87; 530/300; 530/350; 530/387.9; 530/388.1; 530/388.23; 530/388.24; 530/389.1; 530/391.3

(58) Field of Classification Search ......... 530/350, 530/387.9, 388.1, 388.23, 389.1, 391.3, 388.24, 530/380; 435/4, 7.1, 7.21, 7.23; 436/57, 436/86, 87

See application file for complete search history.

(56) References Cited

U.S. PATENT DOCUMENTS

| | | | |
|---|---|---|---|
| 6,297,367 B1 | 10/2001 | Tribouley | 536/23.5 |
| 6,403,770 B1 | 6/2002 | Yu et al. | 530/387.3 |
| 6,475,986 B1 | 11/2002 | Aggarwal | 514/12 |
| 6,475,987 B1 | 11/2002 | Shu | 514/12 |
| 6,541,224 B2 | 4/2003 | Yu et al. | 435/69.5 |
| 6,562,579 B1 * | 5/2003 | Yu et al. | 435/7.1 |
| 6,635,482 B1 | 10/2003 | Yu et al. | 435/326 |
| 6,689,579 B1 * | 2/2004 | Yu et al. | 435/69.1 |
| 6,716,576 B1 | 4/2004 | Yu et al. | 435/6 |
| 6,812,327 B1 | 11/2004 | Yu et al. | 530/351 |
| 6,875,846 B2 | 4/2005 | Rennert et al. | 530/351 |
| 6,881,401 B1 | 4/2005 | Yu et al. | 424/85.1 |
| 7,045,603 B2 | 5/2006 | Goddard et al. | 530/387.9 |
| 2001/0010925 A1 * | 8/2001 | Wiley | 435/69.1 |

FOREIGN PATENT DOCUMENTS

| | | |
|---|---|---|
| WO | WO 99/11791 | 3/1999 |
| WO | WO 99/12964 | 3/1999 |
| WO | WO 99/33980 | 6/1999 |

OTHER PUBLICATIONS

GenCore Database Sheets. Amino Acid Sequence Alignments Between Applicant'SEQ ID No. 1 and Patent's a Patent Application's Sequence 2.*
GenCore database alignment between Applicant'SEQ ID No. 1 and U.S. Patent 6,689,579 B1 (filed Jan. 12, 1998).*
Kimura, Kotohiko et al. Tumor Necrosis Factor-alpha Sensitizes Prostate Cancer Cells to gamma-Irradiation-induced Apoptosis. Cancer Research 59: 1606-1614, Apr. 1, 1999.*
Halicka et al., "2-Deoxy-D-glucose enhances sensitivity of human histiocytic lymphoma U937 cells to apoptosis induced by tumor necrosis factor," *Cancer Res.*, 55:444-449, 1995.
Kaplan et al., "In vitro cytotoxic effects of tumor necrosis factor-alpha in human breast cancer cells may be associated with increased glucose consumption," *FEBS Lett.*, 406:175-178, 1997.
Mukhopadhyay et al. "Identification and characterization of a novel cytokine, THANK, a TNF homologue that activates apoptosis, nulcear factor-kappaB, and c-Jun NH2-terminal kinase," *J. Biol. Chem.*, 274:15978-15981, 1999.
Van Moorselaar et al., "Differential antiproliferative activities of alpha- and gamma-interferon and tumor necrosis factor alone or in combinations against two prostate cancer xenografts transplanted in nude mice," *The Prostate*, 18:331-344, 1991.

* cited by examiner

*Primary Examiner*—Alana M. Harris
(74) *Attorney, Agent, or Firm*—Fulbright & Jaworski L.L.P.

(57) ABSTRACT

The present invention is directed to the applications of a novel cytokine, named THANK, for TNF homologue that activates apoptosis, NF-κB and c-jun N-terminal kinase. Such applications include using THANK inhibitors to inhibit the activation of NF-κB and to treat a pathological condition caused by the activation of NF-κB. Also provided is a method of inhibiting growth of a wide variety of tumor cells by administering THANK protein.

1 Claim, 12 Drawing Sheets

Met Asp Asp Ser Thr Glu Arg Glu Gln Ser Arg Leu Thr Ser Cys
Leu Lys Lys Arg Glu Glu Glu Met Lys Leu Lys Glu Cys Val Ser Ile
Leu Pro Arg Lys Glu Ser Pro Ser Val Arg Ser Ser Lys Asp Gly
Lys Leu Leu Ala Ala Thr Leu Leu Leu Ala Leu Leu Ser Cys Cys
Leu Thr Val Val Ser Phe Tyr Gln Val Ala Ala Leu Gln Gly Asp
Leu Ala Ser Leu Arg Ala Gly Leu Gln Gly His His Ala Glu Lys
Leu Pro Ala Gly Ala Gly Ala Pro Lys Ala Gly Leu Glu Glu Ala
Pro Ala Val Thr Ala Gly Leu Lys Ile Phe Glu Pro Pro Ala Pro
Gly Glu Gly Asn Ser Ser Gln Asn Ser Arg Asn Lys Arg Ala Val
Gln Gly Pro Glu Glu Thr Val Thr Ile Gln Asp Cys Leu Gln Leu Ile
Ala Asp Ser Glu Thr Pro Thr Ile Gln Lys Gly Ser Tyr Thr Phe
Val Pro Trp Leu Leu Ser Phe Lys Arg Gly Ser Ala Leu Glu Glu
Lys Glu Asn Lys Ile Leu Val Lys Glu Thr Gly Tyr Phe Phe Ile
Tyr Gly Gln Val Leu Tyr Thr Asp Lys Thr Tyr Ala Met Gly His
Leu Ile Gln Arg Lys Lys Val His Val Phe Gly Asp Glu Leu Ser
Leu Val Thr Leu Phe Arg Cys Ile Gln Asn Met Pro Glu Thr Leu
Pro Asn Asn Ser Cys Tyr Ser Ala Gly Ile Ala Lys Leu Glu Glu
Gly Asp Glu Leu Gln Leu Ala Ile Pro Arg Glu Asn Ala Gln Ile
Ser Leu Asp Gly Asp Val Thr Phe Phe Gly Ala Leu Lys Leu Leu (SEQ ID No. 1)

Fig. 1

```
  1  MDDSTEREQSRLTSCLKKREEMKLKECVSILPRKESPSVRSSKDGK  46     Intracellular domain
 47  LLAATLLLALLSCCLTVVSFYQVAALQGDLA                 77     Transmembrane domain
 78  SLRAELQGHHAEKLPAGAGAPKAGLEEAPAVTAG 111 AND 112 TO 285   Extracellular domain 1  K I F E P P A P G   - - - - - - E G N S S Q N S R N K R A V Q G   THANK 112-285
  1  - - - - - P G V G L - - - - - - T P S A A Q T A R Q H P K M H L   LT alpha 35-205
  1  - - - - - R S S S R - - - - - - T P S - - - - - - - - - - - - -   TNF alpha 77-233
  1  - - - - - I G H P S P P P P E - S H E - - - - - - - - - - - - -   FasL 130-281
  1  - - - - - I Q E R R - - - - - - S H E - - - - - - - - - - - - -   LIGHT 83-240

L I V Q L

27  P E E T V T Q D C   L Q L I - - A D S E - - - - T P T I Q K G S Y   THANK 112-285
 23  A H S T L K P A -   A H L I - - G D P S - - - - K Q - N S - - - -   LT alpha 35-205
 10  - - - - D K P V -   A H V V - - A N P Q - - - - A E G Q - - - - -   TNF alpha 77-233
 14  - - - - L R K V -   A H L T G   K S N S - - - - R S M P - - - - -   FasL 130-281
 10  - - - - V N P A -   A H L T G A N S S L T G G P - - - - - - - - -   LIGHT 83-240

53  T F V P W L S F     K R G - - S A L E E K E N K   K I L V K E T    THANK 112-285
 43  - - L W R A N T     D R A F L D D G F S L S N D Q L L V P T S     LT alpha 35-205
 26  - - Q W L N R R     A N A L L A N G V E L R D N Q L V V P S E     TNF alpha 77-233
 31  - - L E W E D T     S G V K Y K G V K Y K K G D G A L V I N E T   FasL 130-281
 30  - - L L E T Q L     R G L S Y H D G A L V T K A                   LIGHT 83-240
```

Intracellular domain:     SEQ ID No. 2
Transmembrane domain:     SEQ ID No. 3
Extracellular domain:
    78-111:               SEQ ID No. 4
    112-285:              SEQ ID No. 5

THANK 112-285:      SEQ ID No. 5
LT alpha 35-205:    SEQ ID No. 6
TNF alpha 77-233:   SEQ ID No. 7
FasL 130-281:       SEQ ID No. 8
LIGHT 83-240:       SEQ ID No. 9

USES OF THANK, A TNF HOMOLOGUE THAT ACTIVATES APOPTOSIS

CROSS-REFERENCE TO RELATED APPLICATIONS

This application is a divisional of U.S. Ser. No. 09/496,118, filed Feb. 1, 2000 now U.S. Pat. No. 6,475,986, which in turn claims the benefit of provisional U.S. Ser. No. 60/118,531, filed Feb. 2, 1999, now abandoned.

BACKGROUND OF THE INVENTION

1. Field of the Invention

The present invention relates generally to the fields of biochemistry and molecular oncology. More specifically, the present invention relates to uses of a novel cytokine, THANK, a TNF homologue that activates apoptosis, nuclear Factor-κB, and c-jun N-terminal kinase.

2. Description of the Related Art

In 1984, two homologous cytokines were reported to inhibit the growth of tumor cells specifically (1-7) and was named TNF-α and TNF-β (also called lymphotoxin). Since then over 15 members of this family have been identified, including FasL, CD29L, CD30L, CD40L, OX-40L, 4-1BBL, LT-β, TWEAK, TRAIL, RANKL/TRANCE, LIGHT, VEGI, and APRIL (8-16). At the amino acid sequence level, various members of the TNF family are 20-25% homologous to each other. Most members of this family play an important role in gene activation, proliferation, differentiation, and apoptosis. These ligands interact with the corresponding receptor, also members of the TNF receptor family, and activate the transcription factors NF-κB and AP1 (9, 17), a stress-activated protein kinase (c-jun N-terminal protein kinase, JNK), and a cascade of caspases.

The prior art is deficient in the lack of uses of a novel member of the TNF family, named THANK, for TNF homologue that activates apoptosis, NF-κB, and JNK. For example, the prior art is deficient in the lack of applications of THANK in inhibiting tumor growth and applications of THANK inhibitors in inhibiting the activation of NF-κB. The present invention fulfills this long-standing need and desire in the art.

SUMMARY OF THE INVENTION

By searching an expressed sequence tag (EST) data base using the amino acid sequence motif of TNF, a novel member of the TNF family, named THANK, was identified for TNF homologue that activates apoptosis, NF-κB, and JNK. THANK was primarily expressed by hematopoietic cells. The recombinant THANK activated NF-κB, c-jun N-terminal kinase, caspase-3 and displayed anti-proliferative effects in U937 cells through binding sites distinct from those for TNF.

The present invention is directed to the applications of THANK, including using THANK inhibitors to inhibit the activation of NF-κB and to treat a pathological condition caused by the activation of NF-κB. Also provided is a method of inhibiting growth of a wide variety of tumor cells by administering THANK protein.

In one embodiment of the present invention, there is provided a method of inhibiting the activation of NF-κB in cells by treating the cells with a THANK inhibitor.

In another embodiment of the present invention, there is provided a method of treating a pathological condition caused by the activation of NF-κB in an individual by administering a THANK inhibitor in a therapeutically effective amount. Preferably, the pathological condition is selected from the group consisting of toxic shock, septic shock, acute phase response, viral infection, radiation susceptibility, atherosclerosis, cancer, acute inflammatory conditions, arthritis, allergy, and graft vs. host reaction.

In still another embodiment of the present invention, there is provided a method of inhibiting growth of tumor cells by administering a therapeutically effective amount of THANK protein. Preferably, the cells are selected from the group consisting of myeloid cells, colon cancer cells, prostate cancer cells, breast carcinoma cells, cervical carcinoma cells, chronic myeloid leukemic cells and acute myeloid leukemic cells. Still preferably, THANK protein is administered in a dose of from about 0.01 mg/kg of patient weight per day to about 100 mg/kg of patient weight per day.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the full length amino acid sequence of THANK (SEQ ID No. 1).

Figure 2B:
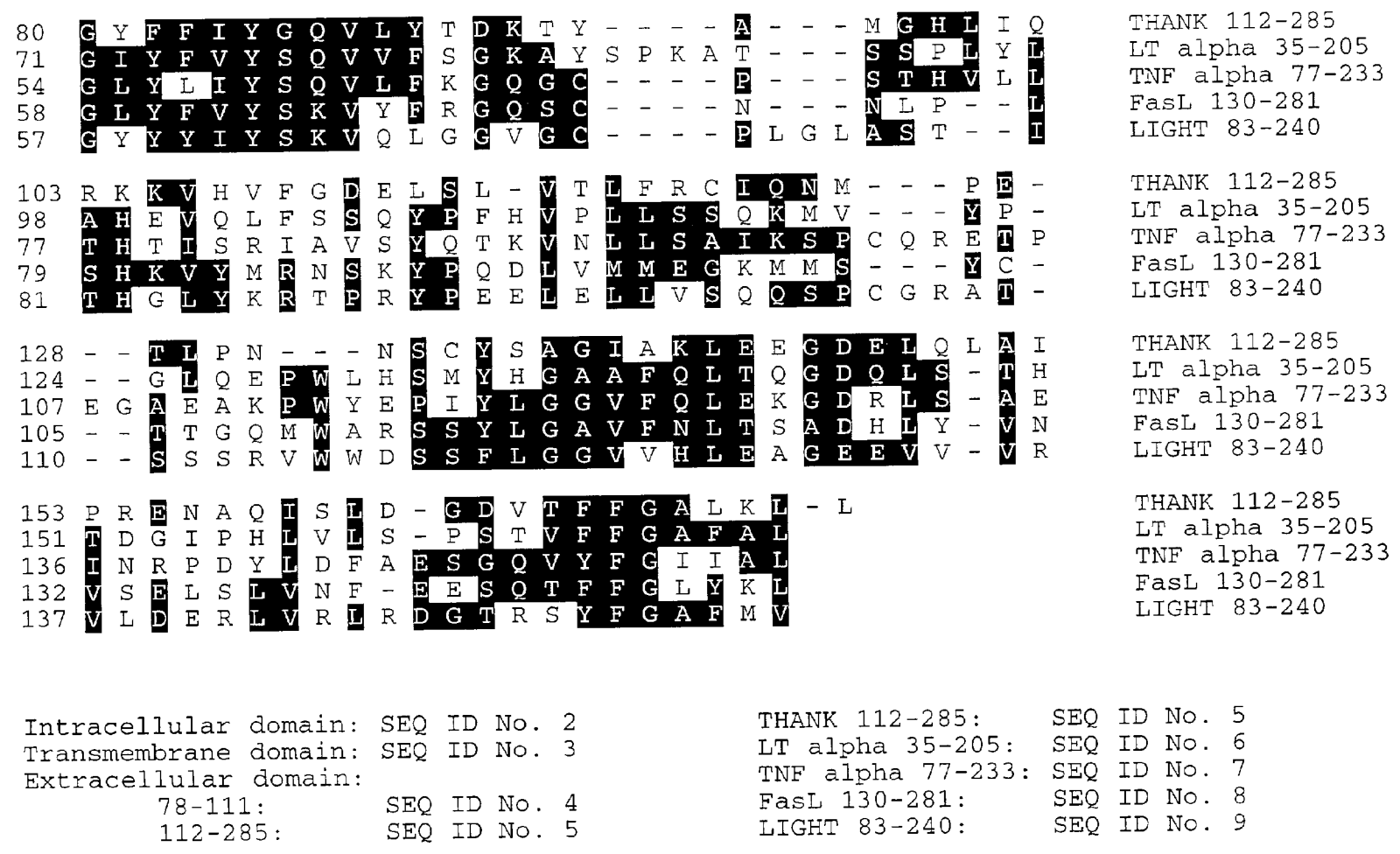

FIGS. 2A and 2B show the amino acid sequence of THANK intracellular domain (SEQ ID No. 2), transmembrane domain (SEQ ID No. 3), extracellular domain (aa 78-111, SEQ ID No. 4) and the comparison of THANK extracellular domain (aa 112-285, SEQ ID No. 5) with mature form of TNF, LT, FasL and LIGHT (SEQ ID Nos. 6-9). Shaded areas indicate homology with LT, TNF, FasL and LIGHT.

DETAILED DESCRIPTION OF THE INVENTION

Figure 2C:
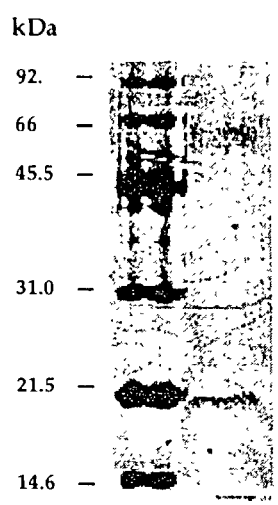
FIG. 2C shows SDS-PAGE analysis of THANK (fraction B).

Using the amino acid sequence motif of TNF, an EST database was searched. A novel full-length cDNA encoding 285 amino acid residues (SEQ ID No. 1, FIG. 1) was identified, and named THANK. THANK is a type II transmembrane protein with 15-20% overall amino acid sequence homology to TNF, LT-α, FasL and LIGHT, all members of the TNF family. The mRNA for THANK was expressed at high levels by peripheral blood leukocytes, lymph node, spleen, and thymus and at low levels by small intestine, pancreas, placenta, and lungs. THANK was also prominently expressed in hematopoietic cell lines. The recombinant purified protein expressed in the baculovirus system had an approximate molecular size 20 kDa with amino terminal sequence of LKIFEPP (SEQ ID No. 10). Treatment of human myeloid U-937 cells with purified THANK activated NF-κB consisting of p50 and p65. Activation was time- and dose-dependent, beginning with as little as 1 pM of the cytokines and as early as 15 min. Under the same conditions, THANK also activated c-jun N-terminal kinase (JNK) in U937 cells. THANK also strongly suppressed the growth of tumor cell lines and activated caspase-3. Although THANK had all the activities and potency of TNF, it did not bind to the TNF receptors, which indicates that THANK is a novel cytokine that belongs to the TNF family and activates apoptosis, NF-κB, and JNK through a distinct receptor.

The present invention is directed to various applications of THANK, including using THANK inhibitors to inhibit the activation of NF-κB and to treat a pathological condition caused by the activation of NF-κB. Also provided is a method of inhibiting growth of a wide variety of tumor cells by administering THANK protein.

In one embodiment of the present invention, there is provided a method of inhibiting the activation of NF-κB in cells by treating the cells with a THANK inhibitor.

In another embodiment of the present invention, there is provided a method of treating a pathological condition caused by the activation of NF-κB in an individual by administering a THANK inhibitor in a therapeutically effective amount. Preferably, the pathological condition is selected from the group consisting of toxic shock, septic shock, acute phase response, viral infection, radiation susceptibility, atherosclerosis, cancer, acute inflammatory conditions, arthritis, allergy, and graft vs. host reaction.

In still another embodiment of the present invention, there is provided a method of inhibiting growth of tumor cells by administering a therapeutically effective amount of the THANK protein. Preferably, the THANK protein is used to treat tumor cells such as myeloid cells, colon cancer cells, prostate cancer cells, breast carcinoma cells, cervical carcinoma cells, chronic myeloid leukemic cells and acute myeloid leukemic cells. Generally, the THANK protein may be adminstered in any pharmacological dose which inhibits or kills tumors. Preferably, the THANK protein is administered in a dose of from about 0.01 mg/kg of patient weight per day to about 100 mg/kg of patient weight per day.

The following examples are given for the purpose of illustrating various embodiments of the invention and are not meant to limit the present invention in any fashion.

EXAMPLE 1

Identification, Cloning, Expression, and Purification of THANK

Using high throughput automated DNA sequence analysis of randomly selected human cDNA clones, a database containing more than two million ESTs obtained from over 750 different cDNA libraries was been generated by Human Genome Sciences, Inc. A specific homology and motif search using the known amino acid sequence motif of TNF family members against this database revealed several ESTs having homology to members of the TNF family. One full length cDNA clone (HNEDU15) encoding an intact N-terminal signal peptide was isolated from a human neutrophil library and selected for further investigation. The complete cDNA sequence of both strands of this clone was determined, and its homology to TNF was confirmed. This gene product was named THANK.

THANK is a 285 amino acid long type II transmembrane protein (SEQ ID No. 1, FIG. 1). The intracellular domain was found to be located between amino acid residues 1 through 46 (SEQ ID No. 2), and the transmembrane domain between amino acid residues 47 through 77 (SEQ ID No. 3) (FIGS. 2A and 2B).

The cDNA encoding the extracellular domain of THANK (aa 78-111, SEQ ID No. 4 and 112-285, SEQ ID No. 5) was amplified employing the PCR technique using the following primers: 5' BamHI, GCGGGATCCCAGCCTCCGGGCA-GAGC (SEQ ID No. 11) and 3' XbaI, GCGTCTAGATCA-CAGCACTTTCAATGC (SEQ ID No. 12). The amplified fragment was purified, digested with BamHI and XbaI, and cloned into a baculovirus expression vector pA2-GP, derived from pVL94. The cloning, expression and confirmation of the identity of the cloned product were performed using standard techniques (18).

Recombinant THANK was purified from the clarified culture supernatant of 92 h post-infected Sf9 cells. The protein was stepwise purified by cation and anion exchange chromatography. The purified THANK was analyzed for purity by 12% SDS-PAGE and by western blot analysis.

EXAMPLE 2

Northern Blot Analysis

Two multiple human tissue northern blots containing 2 µg of poly (A)+ RNA per lane of various tissues (Clontech, Palo Alto, Calif.) were probed with $^{32}$P-labeled THANK cDNA. RNA from a selected panel of human cell lines were probed following the same technique.

EXAMPLE 3

Production of THANK Antibodies

Antibodies against THANK were raised by injecting 0.2 mg purified recombinant antigen in Freund's complete adjuvant (Difco Laboratories) subcutaneously into a rabbit. After three weeks, the injection was repeated and the rabbit was bled every third week. The specificity of the antiserum was tested by ELISA and western blot.

EXAMPLE 4

Receptor-Binding Assay

TNF receptor-binding assay was performed following a modified procedure previously described (19). Briefly, 0.5× $10^6$ cells/well (triplicate well) in 100 µl binding medium (RPMI-1640 containing 10% FBS) were incubated with $^{125}$I-labelled TNF ($2.5\times10^5$ cpm/well, specific activity 40 mCi/mg) either alone (total binding) or in the presence of 20 nM unlabeled TNF (nonspecific binding) or 150 nM unlabeled THANK in an ice bath for 1 h. Thereafter, cells were washed three times with ice-cold PBS containing 0.1% BSA to remove unbound $^{125}$I-TNF. The cells were dried at 80° C., and the cell bound radioactivity was determined in a gamma counter (Cobra-Auto Gamma, Packard Instrument Co.)

EXAMPLE 5

Electrophoretic Mobility Shift Assay (EMSA)

NF-κB activation was analyzed by EMSA as described previously (20, 21). In brief, 6 µg nuclear extracts prepared from THANK-treated cells were incubated with $^{32}$P-end-labeled 45-mer double-stranded NF-κB oligonucleotide for 15 min at 37° C., and the DNA-protein complex resolved in 7.5% native polyacrylamide gel. The specificity of binding was examined by competition with unlabeled 100-fold excess oligonucleotide. The specificity of binding was also determined by supershift of the DNA-protein complex using specific and irrelevant antibodies. The samples of supershift experiments were resolved on 5.5% native gels. The radioactive bands from dried gels were visualized and quantitated by PhosphorImager (Molecular Dynamics, Sunnyvale, Calif.) using ImageQuant software.

EXAMPLE 6

Western Blot of THANK

Purified THANK sample was resolved on 12% SDS-PAGE, electrotransferred to a nitrocellulose membrane, and probed with polyclonal antibodies (1:6000) raised in rabbits. The blot was then treated with HRP-conjugated secondary antibodies and finally detected by chemiluminescence (ECL, Amersham Pharmacia Biotech. Arlington Heights, Ill.).

EXAMPLE 7 c-Jun Kinase Assay

The c-Jun kinase assay was performed by a modified method as described earlier (22). Briefly, 100-µg cytoplasmic extracts were treated with anti-JNK1 antibodies, the immunocomplexes were precipitated with protein A/G-Sepharose beads (Pierce, Rockford, Ill.) and assayed for the enzymatic activity by using glutathione S-transferase-Jun (aa 1-79) as substrate (2 µg) in the presence of 10 µCi [$^{32}$P]ATP. The kinase reaction was carried out by incubating the above mixture at 30° C. in kinase assay buffer for 15 minutes. The reaction was stopped by adding SDS sample buffer, followed by boiling. Finally, protein was resolved on a 9% acrylamide gel under reduced conditions. The radioactive bands of the dried gel were visualized and quantitated by phosphorImager as mentioned previously.

To determine the total amount of JNK1 protein, 30 µg of the cytoplasmic extracts were loaded on 9% acrylamide gels. After electrophoresis, the protein was transferred to nitrocellulose membranes, blocked with 5% non-fat milk protein and probed with rabbit polyclonal antibodies (1:3000) against JNK1. The blots were then reacted with HRP-conjugated secondary antibodies and finally detected by chemiluminescence (ECL, Amersham)

EXAMPLE 8

Cytotoxicity Assays

The cytotoxic effects of THANK against tumor cells were measured by modified tetrazolium salt (MTT) assay described earlier (23) and by its ability to activate caspase-3 leading to cleavage of poly (ADP-ribose) polymerase (PARP) (24). For cytotoxicity, $5\times10^3$ cells in 0.1 ml were plated in triplicate in 96-well plates and exposed to variable concentrations of either THANK or TNF (for comparison) in 0.1 ml. After 72 h incubation at 37° C., cells were examined for viability. To estimate caspase-3 activation by PARP cleavage, cell extracts (50 µg/sample) were resolved on 7.5% acrylamide gels, electrophoresed, transferred to nitrocellulose membranes, blocked with 5% non-fat milk protein, probed with PARP monoclonal antibody (1:3000) and detected by ECL as indicated above.

EXAMPLE 9

Identification, Sequence, and Purification of THANK

Figure 2D:
FIG. 2D shows western blot analysis of THANK (fraction B).

The predicted amino acid sequence of mature THANK (112-285, SEQ ID No. 5) is 15%, 16%, 18% and 19% identical to LIGHT, FasL, TNF arid LT-α, respectively (FIGS. 2A and 2B). The cDNA for this novel cytokine was cloned and expressed in a baculovirus expression system. In CM cellulose cation-exchange chromatography, THANK eluted first with 1 M NaCl (fraction A) and then with 1.5 M NaCl (fraction B). Fractions A and B had approximate molecular mass of 23 kDa and 20 kDa, respectively on 12% SDS-PAGE (FIG. 2C); and amino terminal sequences of LKIFEPP (SEQ ID No. 10) and AVQGP (SEQ ID No. 13) starting at AA112 and AA134, respectively. An apparently higher molecular size obtained by SDS-PAGE than that predicted from the number of amino acids suggested a post-translational modification. The amino acid sequence of the mature THANK lacked, however, the potential N-glycosylatio site. Polyclonal antibodies prepared against THANK recognized the cytokine on western blot (FIG. 2D).

EXAMPLE 10

Tissue and Cell Line Distribution of THANK

Figure 2E:
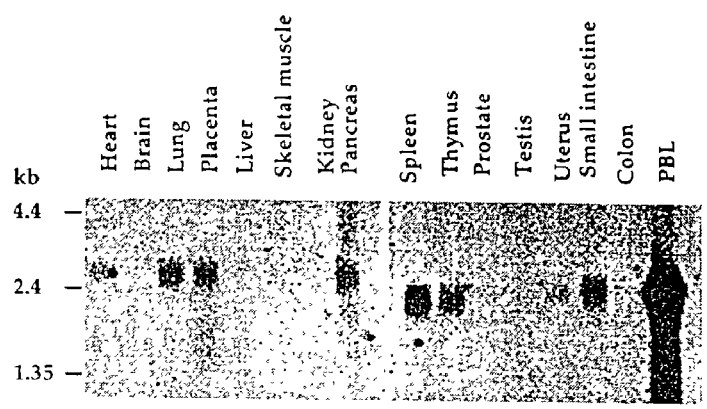
FIG. 2E shows tissue distribution of THANK mRNA.
Figure 2F:
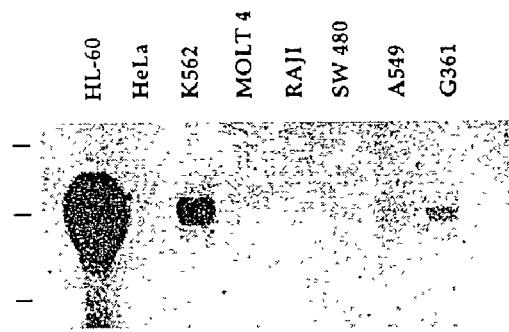
FIG. 2F shows the expression of THANK mRNA by various cell lines. PBL, perepheral blood leucocytes.

Northern blot analysis indicated that THANK was expressed in peripheral blood leukocytes (PBL), spleen, thymus, lung, placenta, small intestine and pancreas; with highest expression in PBL (FIG. 2E). Analysis of the cell line blot (Clonetech Inc.) revealed very high expression in HL60, detectable expression in K562, A549, and G361, and no detectable transcript in HeLa, MOLT4, Raji, and SW480 cell lines. Thus cells and tissues of the immune system expressed THANK transcripts.

EXAMPLE 11

THANK Activates NF-κB

Figure 3A:
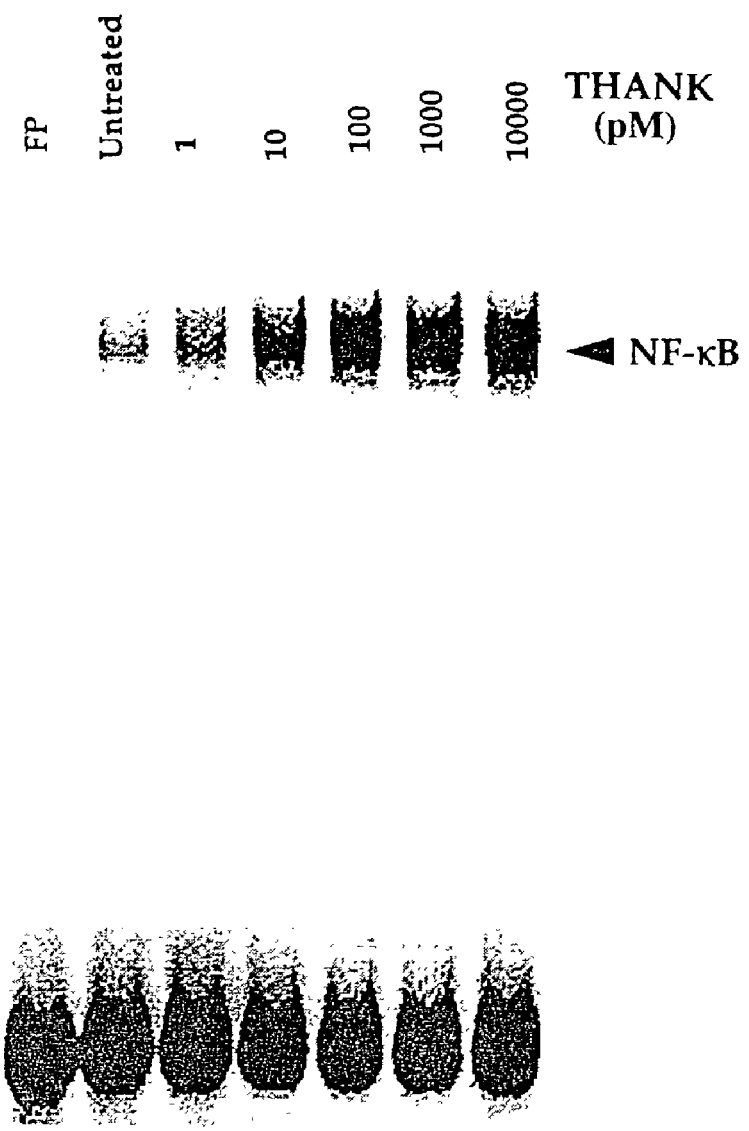
FIG. 3A shows the dose response of THANK-induced NF-κB activation. U937 cells (2×10$^6$/ml) were treated with different concentrations of THANK for 60 min at 37° C. and then assayed for NF-κB by EMSA.
Figure 3B:
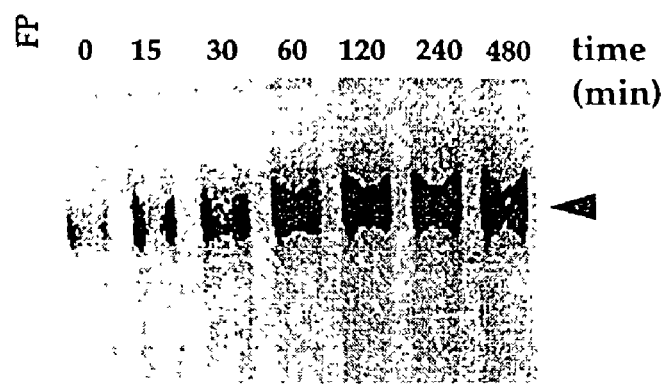
FIG. 3B shows kinetics of NF-κB activation. U937 cells (2×10$^6$/ml) were treated with 1 nM of THANK for various lengths of time.
Figure 3C:
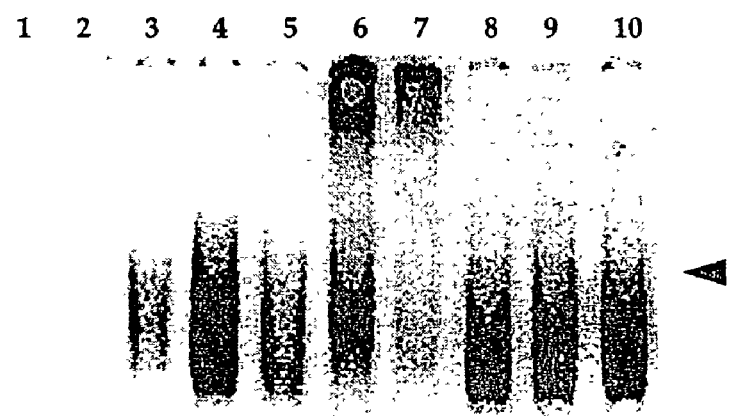
FIG. 3C shows supershift and specificity of NF-κB. Nuclear extract of THANK treated cells (lane 4) were incubated at room temperature for 60 min with anti-p50 (lane 5), anti-p65 (lane 6), mixture of anti-p50 and anti-p65 (lane 7), anti-c-Rel (lane 8), anti-cyclin D1 (lane 9), preimmune serum (lane 10), unlabeled NF-κB oligo nucleotide (lane 2) and then assayed for NF-κB. Lane 1 shows results for free probe, and lanes 3 and 4 show the THANK-untreated and treated cells, respectively.

One of the earliest events activated by most members of the TNF superfamily is NF-κB activation (25). The results depicted in FIGS. 3A & 3B indicate that THANK activated NF-κB in a dose and time-dependent manner. Less that 10 pM THANK was enough to activate NF-κB in U937 cells, though peak activation was obtained at 1 nM (FIG. 3A). THANK induced optimum NF-κB activation within 60 min at 1 nM; no significant increase was thereafter (FIG. 3B). The gel shift band was specific, as its formation could be eliminated with excess unlabeled oligonucleotide. It was supershifted by anti-p50 and anti-p65 antibodies only (FIG. 3C), thus indicating that the nuclear factor was composed of p50 and $p^{65}$ subunits. No significant difference was found in the ability to activate NF-κB between 20 and 23 kDa forms of THANK indicating that residues 112 through 134 are optional for the biological activity (data not shown).

Figure 3D:
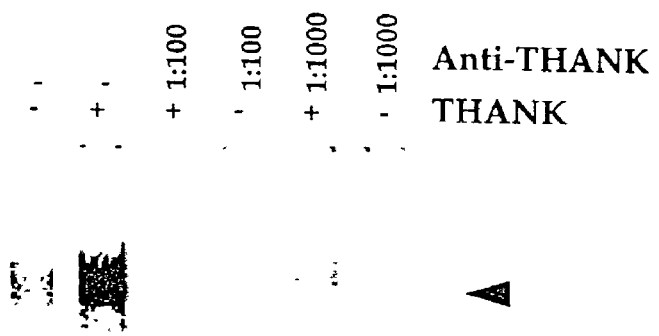
FIG. 3D shows effect of anti-THANK polyclonal antibodies on THANK-induced NF-κB activation in U937 cells. THANK was preincubated with anti-THANK antibodies at a dilution of 1:100 or 1:1000 before cells were exposed.
Figure 3E:
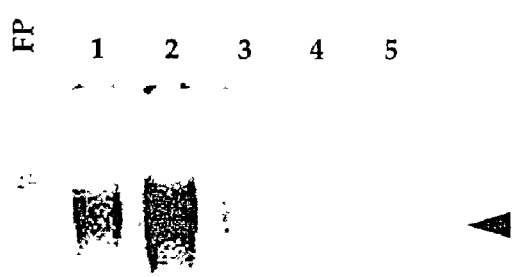
FIG. 3E shows effect of trypsinization and heat denaturation on the ability of THANK to activate NF-κB in U937 cells. THANK was treated with 0.25% trypsin at 37° C. for 60 min and then checked for its ability to activate NF-κB (lane 3). The effect of trypsin alone is shown in lane 4. THANK was boiled at 100° C. for 10 min, and used for the activation of NF-κB (lane 5). Lane 1 and lane 2 represent NF-κB activation for untreated and THANK treated U937 cells, respectively.

To ascertain that the observed activation was due to THANK and not a contaminant, the protein was preincubated with anti-THANK polyclonal antibodies before treatment with the cells. FIG. 3D shows a lack of NF-κB activation after treatment of THANK with antibodies even at a 1 to 1000 dilution. Antibody against THANK by itself had no effect. To further ascertain that NF-κB activation was due to the proteinaceous nature of THANK, the protein was either digested with trypsin or heat-denatured prior to treatment. Both treatments completely abolished NF-κB activation in U937 cells, confirming that THANK was responsible for this activation (FIG. 3E). Although THANK was as potent as TNF with respect to both dose and time required for NF-κB activation, the overall amplitude of response was less with THANK. In this respect the activity of THANK was comparable with LT-α (21).

EXAMPLE 12

THANK Activates c-Jun N-terminal Kinase

Figure 4A:
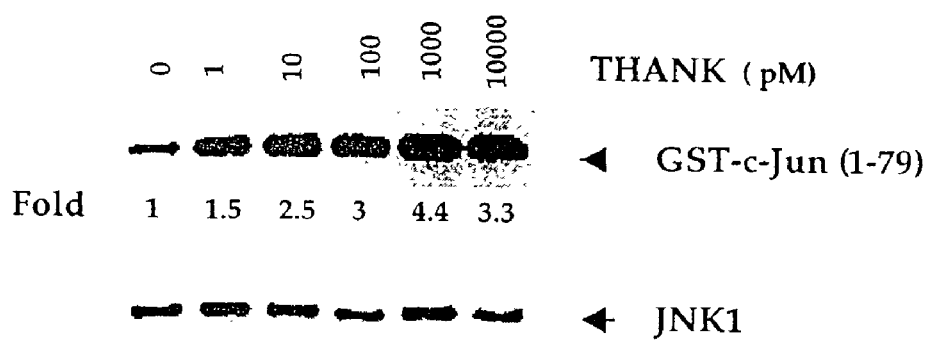
FIG. 4A shows the dose response of THANK-induced JNK activation. U937 cells ($2 \times 10^6$/ml) were treated with different concentrations of THANK for 1 h at 37° C. and assayed for JNK activation as described in the methods. Lower panel shows equal loading of protein.
Figure 4B:
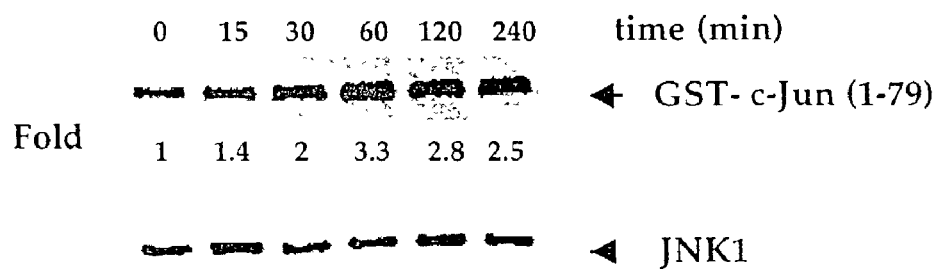
FIG. 4B shows kinetics of THANK-induced activation of JNK. U937 cells ($2 \times 10^6$/ml) were treated with 1 nM THANK for indicated time period and assayed for JNK activation. Lower panel shows equal loading of protein.

The activation of c-Jun kinase (JNK) is another early event that is initiated by different members of the TNF family (17, 22). THANK activated JNK activity in a time- and dose-dependent manner (FIGS. 4A & 4B). At 10 pM the activity increased by 2.5-fold; at 1 nM it reached 4.4 fold. An additional increase in THANK concentration slightly decreased activation (FIG. 4A). The peak activation of JNK was observed at 60 min (3.3-fold increase), which gradually decreased thereafter (FIG. 4B). These results suggest that, like TNF, THANK transiently activates JNK in U937 cells. The activation of JNK by THANK was not due to an increase in JNK protein levels, as immunoblot analysis demonstrated comparable JNK1 expression at all dose and time points (FIGS. 4A & 4B, lower panels)

EXAMPLE 13

THANK-Induced Cytotoxicity and Caspase-3 Activation

Activations of NF-κB and JNK are early cellular responses to TNF, which are followed by cytotoxic effects to tumor cells. The effect of different concentrations of THANK on the cytotoxic effects against tumor cell lines was examined and compared with that of TNF.

Figure 5A:
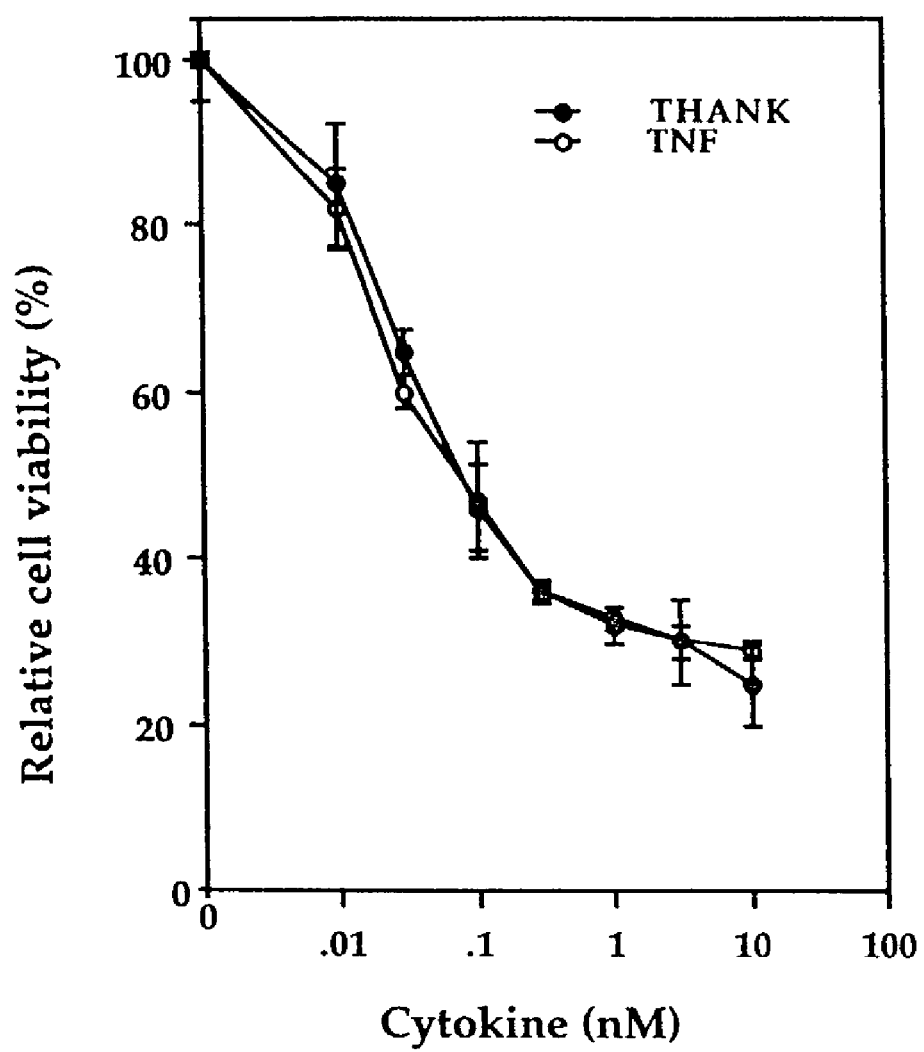
FIG. 5A shows the dose-dependent cytotoxic effects of THANK against U937 cells. $5 \times 10^3$ cells/well were incubated in triplicate with various concentrations of THANK and then examined for cell viability after 72 hours. Untreated control is expressed as 100%.

Results in FIG. 5A show that THANK inhibited the growth of human histiocytic lymphoma U-937 cells in a dose-dependent manner. Besides U-937 cells, THANK also inhibited the growth of prostate cancer (PC-3) cells, colon cancer cells (HT-29), cervical carcinoma cells (HeLa), breast carcinoma cells (MCF-7), and embryonic kidney cells (A293) (data not shown). The growth inhibition curve of THANK was superimposable with that of TNF, indicating comparable potency.

Figure 5B:
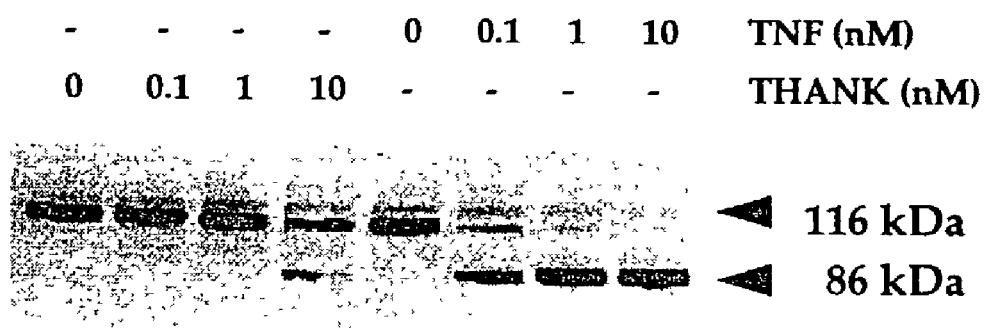
FIG. 5B shows THANK-induced cleavage of PARP in U937 cells. U937 cells ($2 \times 10^6$ cells/ml) were treated with 0.1, 1 and 10 nM THANK in presence of cycloheximide (10 μg/ml) for 2 hours at 37° C. In order to compare the cleavage, TNF was used as a positive control.

Degradation of PARP by caspase-3 is one of the hallmarks of apoptosis in tumor cells (26). It was found that treatment of U-937 cells with THANK for 2 h induced partial cleavage of PARP in U937 cells, whereas TNF almost completely cleaved PARP under these conditions (FIG. 5B). This suggests that THANK can activate caspase-3, though not so strongly as TNF.

EXAMPLE 14

THANK Binds to Receptors Distinct from TNF Receptors

Figure 5C:
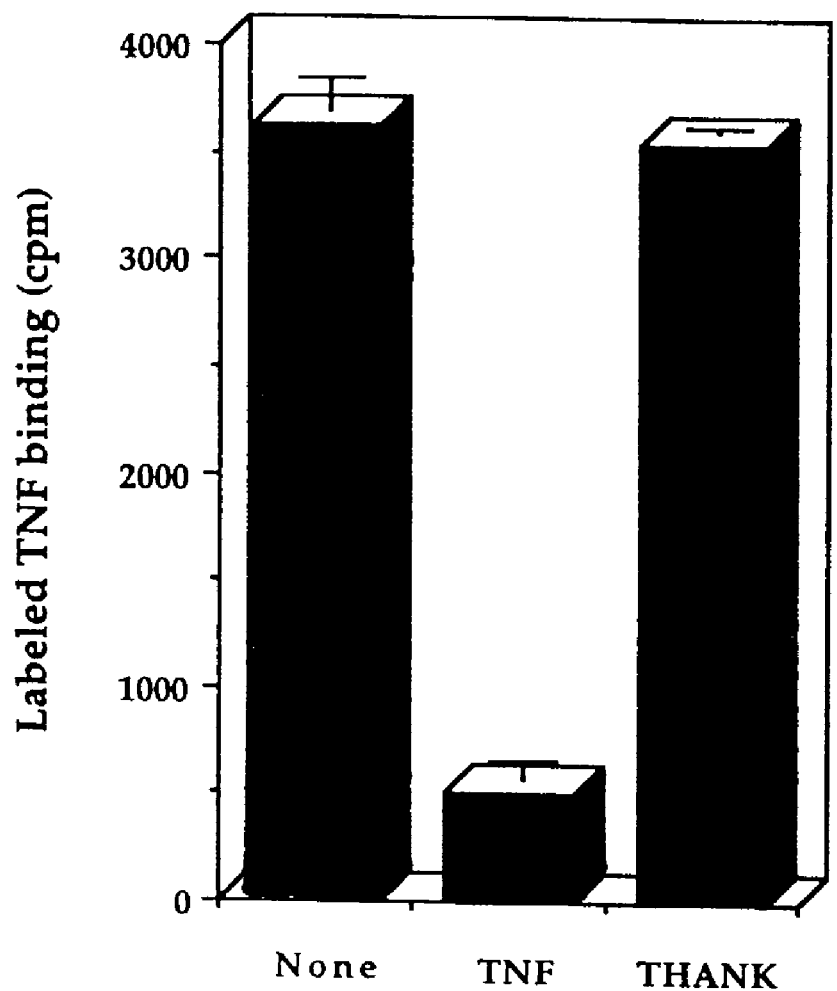
FIG. 5C shows competitive inhibition of labeled TNF binding to U937 cells by unlabeled TNF (20 nM) and THANK (150 nM). U937 cells ($0.5 \times 10^6$ cells/well) were incubated with $0.25 \times 10^6$ cpm of $^{125}$I-TNF in ice bath for 1 hour in presence or absence of the unlabeled competitors. Cell-bound radioactivity was measured in a gamma counter. Results are expressed as mean±S.D.

It was previously shown that TNF and LT, which share homology with each other to the same extent as THANK, bind to the same cell surface receptors (4). Since THANK has significant amino acid sequence homology with TNF, and like TNF exhibits cytotoxic effects, and activates NF-κB and JNK, its binding to the TNF receptor was examined. The receptor binding results (FIG. 5C) show that 20 nM unlabeled TNF almost completely blocked the binding of $^{125}$I-labeled TNF to U-937 cells, whereas 150 nM unlabeled THANK did not compete for $^{125}$I-TNF binding sites. These results suggest that THANK interacts with U937 cells through a receptor distinct from that for TNF.

In summary, a novel cytokine expressed by hematopoietic cells was identified, which can, like TNF and LT-α, activate NF-κB and JNK and inhibit the growth of a wide variety of tumor cells. Although the structure of THANK also exhibits homology to FasL and LIGHT, the latter have not been reported to activate NF-κB. Preliminary results by using flow cytometry indicate that THANK protein is expressed by promyelomonocytic HL-60 cells (data not shown). Because THANK is expressed by hematopoietic cells, it appears to be similar to LT-α and dissimilar from other members of the TNF superfamily. Among all the members of the TNF superfamily, THANK exhibits cytotoxic effects similar to TNF and LT-α. Whether THANK exhibits immunomodulatory activities and in vivo antitumor activities is currently under investigation.

The following references were cited herewith.
1. Aggarwal, et al., 1984 *J Biol Chem*, 259:686-691.
2. Gray, et al., 1984 *Nature*, 312:721-724.
3. Pennica, et al., 1984 *Nature*, 312:724-729.
4. Aggarwal, et al., 1985 *Nature*, 318:665-667.
5. Aggarwal, et al., 1985 *J Biol Chem*, 260:2334-2344.
6. Aggarwal, et al., *J Biol Chem*, 260:2345-2354.
7. Sugarman, et al., 1985 *Science*, 230:943-945.
8. Aggarwal, et al., 1996 *Eur. Cytokine Netw.* 7: 93-124.
9. Smith, et al., 1994 *Cell* 76: 959-962.
10. Wiley, et al., 1995 *Immunity.* 8:21-30.
12. Hahne, et al., 1998. *J. Exp. Med.* 188:1185-90.
13. Chicheportiche, et al., *J. Biol. Chem.* 272: 32401-32410.
14. Zhai, et al., *FASEB J.* (In press).
15. Anderson, et al., *Nature.* 390:175-9.
16. Wong, et al., *J. Biol. Chem.* 272: 25190-4.
17. Singh, et al., 1998 *J. Interferon and Cytokine Res.* 18, 439-450.
18. Ni, et al., 1997 *J. Biol. Chem.* 272: 10853-10858.
19. Higuchi, et al., 1992 *Anal. Biochem.* 204: 53-57.
20. Schreiber, et al., 1989 *Nucleic Acids Res.* 17: 6419-6422.
21. Chaturvedi, et al., 1994 *J. Biol. Chem.* 269: 14575-14583.
22. Kumar, et al., 1998. *Methods in Enzymology*, Vol. 000 (ed. L. Packer), Academic Press, pp. 339-345.
23. Hansen, et al., 1989 *J. Immunol. Methods.* 119: 203-210.
24. Haridas, et al., 1998 *J. Immunol.* 160, 3152-3162.
25. Baeuerle, et al., 1996 *Cell* 87:13-20.
26. Tewari, et al., 1995. *Cell* 81:801-9.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

---

What is claimed is:

1. A method of inhibiting the activation of nuclear factor-κB in cancer cells to thereby induce radiation susceptibility therein, comprising the steps of treating said cells with an inhibitor of THANK protein in an amount effective to induce radiation sensitivity therein, wherein the THANK inhibitor is an antibody that recognizes THANK protein, and wherein said THANK protein is defined by the amino acid sequence of SEQ ID NO:1.

* * * * *

SEQUENCE LISTING

```
<160> NUMBER OF SEQ ID NOS: 13

<210> SEQ ID NO 1
<211> LENGTH: 285
<212> TYPE: PRT
<213> ORGANISM: Homo sapiens
<220> FEATURE:
<223> OTHER INFORMATION: amino acid sequence of THANK protein

<400> SEQUENCE: 1

Met Asp Asp Ser Thr Glu Arg Glu Gln Ser Arg Leu Thr Ser Cys
                 5                  10                  15

Leu Lys Lys Arg Glu Glu Met Lys Leu Lys Glu Cys Val Ser Ile
                20                  25                  30

Leu Pro Arg Lys Glu Ser Pro Ser Val Arg Ser Ser Lys Asp Gly
                35                  40                  45

Lys Leu Leu Ala Ala Thr Leu Leu Leu Ala Leu Leu Ser Cys Cys
                50                  55                  60

Leu Thr Val Val Ser Phe Tyr Gln Val Ala Ala Leu Gln Gly Asp
                65                  70                  75

Leu Ala Ser Leu Arg Ala Glu Leu Gln Gly His His Ala Glu Lys
                80                  85                  90

Leu Pro Ala Gly Ala Gly Ala Pro Lys Ala Gly Leu Glu Glu Ala
                95                 100                 105

Pro Ala Val Thr Ala Gly Leu Lys Ile Phe Glu Pro Pro Ala Pro
               110                 115                 120

Gly Glu Gly Asn Ser Ser Gln Asn Ser Arg Asn Lys Arg Ala Val
               125                 130                 135

Gln Gly Pro Glu Glu Thr Val Thr Gln Asp Cys Leu Gln Leu Ile
               140                 145                 150

Ala Asp Ser Glu Thr Pro Thr Ile Gln Lys Gly Ser Tyr Thr Phe
```

```
                    155                 160                 165
Val Pro Trp Leu Leu Ser Phe Lys Arg Gly Ser Ala Leu Glu Glu
                170                 175                 180

Lys Glu Asn Lys Ile Leu Val Lys Glu Thr Gly Tyr Phe Phe Ile
                185                 190                 195

Tyr Gly Gln Val Leu Tyr Thr Asp Lys Thr Tyr Ala Met Gly His
                200                 205                 210

Leu Ile Gln Arg Lys Lys Val His Val Phe Gly Asp Glu Leu Ser
                215                 220                 225

Leu Val Thr Leu Phe Arg Cys Ile Gln Asn Met Pro Glu Thr Leu
                230                 235                 240

Pro Asn Asn Ser Cys Tyr Ser Ala Gly Ile Ala Lys Leu Glu Glu
                245                 250                 255

Gly Asp Glu Leu Gln Leu Ala Ile Pro Arg Glu Asn Ala Gln Ile
                260                 265                 270

Ser Leu Asp Gly Asp Val Thr Phe Phe Gly Ala Leu Lys Leu Leu
                275                 280                 285

<210> SEQ ID NO 2
<211> LENGTH: 46
<212> TYPE: PRT
<213> ORGANISM: Homo sapiens
<220> FEATURE:
<221> NAME/KEY: domain
<222> LOCATION: 1..46
<223> OTHER INFORMATION: sequence of THANK intracellular domain

<400> SEQUENCE: 2

Met Asp Asp Ser Thr Glu Arg Glu Gln Ser Arg Leu Thr Ser Cys
                  5                  10                  15

Leu Lys Lys Arg Glu Glu Met Lys Leu Lys Glu Cys Val Ser Ile
                 20                  25                  30

Leu Pro Arg Lys Glu Ser Pro Ser Val Arg Ser Ser Lys Asp Gly
                 35                  40                  45

Lys

<210> SEQ ID NO 3
<211> LENGTH: 31
<212> TYPE: PRT
<213> ORGANISM: Homo sapiens
<220> FEATURE:
<221> NAME/KEY: domain
<222> LOCATION: 47..77
<223> OTHER INFORMATION: sequence of THANK transmembrane domain

<400> SEQUENCE: 3

Leu Leu Ala Ala Thr Leu Leu Leu Ala Leu Leu Ser Cys Cys Leu
                  5                  10                  15

Thr Val Val Ser Phe Tyr Gln Val Ala Ala Leu Gln Gly Asp Leu
                 20                  25                  30

Ala

<210> SEQ ID NO 4
<211> LENGTH: 34
<212> TYPE: PRT
<213> ORGANISM: Homo sapiens
<220> FEATURE:
<221> NAME/KEY: domain
<222> LOCATION: 78..111
<223> OTHER INFORMATION: sequence of THANK extracellular domain
```

```
<400> SEQUENCE: 4

Ser Leu Arg Ala Glu Leu Gln Gly His His Ala Glu Lys Leu Pro
                5                  10                  15

Ala Gly Ala Gly Ala Pro Lys Ala Gly Leu Glu Glu Ala Pro Ala
                20                  25                  30

Val Thr Ala Gly

<210> SEQ ID NO 5
<211> LENGTH: 174
<212> TYPE: PRT
<213> ORGANISM: Homo sapiens
<220> FEATURE:
<221> NAME/KEY: domain
<222> LOCATION: 112..285
<223> OTHER INFORMATION: sequence of THANK extracellular domain

<400> SEQUENCE: 5

Leu Lys Ile Phe Glu Pro Pro Ala Pro Gly Glu Gly Asn Ser Ser
                5                  10                  15

Gln Asn Ser Arg Asn Lys Arg Ala Val Gln Gly Pro Glu Glu Thr
                20                  25                  30

Val Thr Gln Asp Cys Leu Gln Leu Ile Ala Asp Ser Glu Thr Pro
                35                  40                  45

Thr Ile Gln Lys Gly Ser Tyr Thr Phe Val Pro Trp Leu Leu Ser
                50                  55                  60

Phe Lys Arg Gly Ser Ala Leu Glu Glu Lys Glu Asn Lys Ile Leu
                65                  70                  75

Val Lys Glu Thr Gly Tyr Phe Phe Ile Tyr Gly Gln Val Leu Tyr
                80                  85                  90

Thr Asp Lys Thr Tyr Ala Met Gly His Leu Ile Gln Arg Lys Lys
                95                 100                 105

Val His Val Phe Gly Asp Glu Leu Ser Leu Val Thr Leu Phe Arg
               110                 115                 120

Cys Ile Gln Asn Met Pro Glu Thr Leu Pro Asn Asn Ser Cys Tyr
               125                 130                 135

Ser Ala Gly Ile Ala Lys Leu Glu Glu Gly Asp Glu Leu Gln Leu
               140                 145                 150

Ala Ile Pro Arg Glu Asn Ala Gln Ile Ser Leu Asp Gly Asp Val
               155                 160                 165

Thr Phe Phe Gly Ala Leu Lys Leu Leu
               170

<210> SEQ ID NO 6
<211> LENGTH: 171
<212> TYPE: PRT
<213> ORGANISM: Homo sapiens
<220> FEATURE:
<221> NAME/KEY: domain
<222> LOCATION: 35..205
<223> OTHER INFORMATION: sequence of mature form of LT-(

<400> SEQUENCE: 6

Leu Pro Gly Val Gly Leu Thr Pro Ser Ala Ala Gln Thr Ala Arg
                5                  10                  15

Gln His Pro Lys Met His Leu Ala His Ser Thr Leu Lys Pro Ala
                20                  25                  30

Ala His Leu Ile Gly Asp Pro Ser Lys Gln Asn Ser Leu Leu Trp
                35                  40                  45
```

-continued

```
Arg Ala Asn Thr Asp Arg Ala Phe Leu Gln Asp Gly Phe Ser Leu
                50                  55                  60

Ser Asn Asn Ser Leu Leu Val Pro Thr Ser Gly Ile Tyr Phe Val
                65                  70                  75

Tyr Ser Gln Val Val Phe Ser Gly Lys Ala Tyr Ser Pro Lys Ala
                80                  85                  90

Thr Ser Ser Pro Leu Tyr Leu Ala His Glu Val Gln Leu Phe Ser
                95                 100                 105

Ser Gln Tyr Pro Phe His Val Pro Leu Leu Ser Ser Gln Lys Met
               110                 115                 120

Val Tyr Pro Gly Leu Gln Glu Pro Trp Leu His Ser Met Tyr His
               125                 130                 135

Gly Ala Ala Phe Gln Leu Thr Gln Gly Asp Gln Leu Ser Thr His
               140                 145                 150

Thr Asp Gly Ile Pro His Leu Val Leu Ser Pro Ser Thr Val Phe
               155                 160                 165

Phe Gly Ala Phe Ala Leu
               170

<210> SEQ ID NO 7
<211> LENGTH: 157
<212> TYPE: PRT
<213> ORGANISM: Homo sapiens
<220> FEATURE:
<221> NAME/KEY: domain
<222> LOCATION: 77..233
<223> OTHER INFORMATION: sequence of mature form of TNF-(

<400> SEQUENCE: 7

Val Arg Ser Ser Ser Arg Thr Pro Ser Asp Lys Pro Val Ala His
                 5                  10                  15

Val Val Ala Asn Pro Gln Ala Glu Gly Gln Leu Gln Trp Leu Asn
                20                  25                  30

Arg Arg Ala Asn Ala Leu Leu Ala Asn Gly Val Glu Leu Arg Asp
                35                  40                  45

Asn Gln Leu Val Val Pro Ser Glu Gly Leu Tyr Leu Ile Tyr Ser
                50                  55                  60

Gln Val Leu Phe Lys Gly Gln Gly Cys Pro Ser Thr His Val Leu
                65                  70                  75

Leu Thr His Thr Ile Ser Arg Ile Ala Val Ser Tyr Gln Thr Lys
                80                  85                  90

Val Asn Leu Leu Ser Ala Ile Lys Ser Pro Cys Gln Arg Glu Thr
                95                 100                 105

Pro Glu Gly Ala Glu Ala Lys Pro Trp Tyr Glu Pro Ile Tyr Leu
               110                 115                 120

Gly Gly Val Phe Gln Leu Glu Lys Gly Asp Arg Leu Ser Ala Glu
               125                 130                 135

Ile Asn Arg Pro Asp Tyr Leu Asp Phe Ala Glu Ser Gly Gln Val
               140                 145                 150

Tyr Phe Gly Ile Ile Ala Leu
               155

<210> SEQ ID NO 8
<211> LENGTH: 152
<212> TYPE: PRT
<213> ORGANISM: Homo sapiens
<220> FEATURE:
<221> NAME/KEY: domain
```

```
<222> LOCATION: 130..281
<223> OTHER INFORMATION: sequence of mature form of FasL

<400> SEQUENCE: 8
```

Gln Ile Gly His Pro Ser Pro Pro Glu Lys Lys Glu Leu Arg
                    5                  10                 15

Lys Val Ala His Leu Thr Gly Lys Ser Asn Ser Arg Ser Met Pro
                20                  25                  30

Leu Glu Trp Glu Asp Thr Tyr Gly Ile Val Leu Leu Ser Gly Val
                35                  40                  45

Lys Tyr Lys Lys Gly Gly Leu Val Ile Asn Glu Thr Gly Leu Tyr
                50                  55                  60

Phe Val Tyr Ser Lys Val Tyr Phe Arg Gly Gln Ser Cys Asn Asn
                65                  70                  75

Leu Pro Leu Ser His Lys Val Tyr Met Arg Asn Ser Lys Tyr Pro
                80                  85                  90

Gln Asp Leu Val Met Met Glu Gly Lys Met Met Ser Tyr Cys Thr
                95                  100                 105

Thr Gly Gln Met Trp Ala Arg Ser Ser Tyr Leu Gly Ala Val Phe
                110                 115                 120

Asn Leu Thr Ser Ala Asp His Leu Tyr Val Asn Val Ser Glu Leu
                125                 130                 135

Ser Leu Val Asn Phe Glu Glu Ser Gln Thr Phe Phe Gly Leu Tyr
                140                 145                 150

Lys Leu

```
<210> SEQ ID NO 9
<211> LENGTH: 158
<212> TYPE: PRT
<213> ORGANISM: Homo sapiens
<220> FEATURE:
<221> NAME/KEY: domain
<222> LOCATION: 83..240
<223> OTHER INFORMATION: sequence of mature form of LIGHT

<400> SEQUENCE: 9
```

Leu Ile Gln Glu Arg Arg Ser His Glu Val Asn Pro Ala Ala His
                    5                  10                 15

Leu Thr Gly Ala Asn Ser Ser Leu Thr Gly Ser Gly Gly Pro Leu
                20                  25                  30

Leu Trp Glu Thr Gln Leu Gly Leu Ala Phe Leu Arg Gly Leu Ser
                35                  40                  45

Tyr His Asp Gly Ala Leu Val Val Thr Lys Ala Gly Tyr Tyr Tyr
                50                  55                  60

Ile Tyr Ser Lys Val Gln Leu Gly Gly Val Gly Cys Pro Leu Gly
                65                  70                  75

Leu Ala Ser Thr Ile Thr His Gly Leu Tyr Lys Arg Thr Pro Arg
                80                  85                  90

Tyr Pro Glu Glu Leu Glu Leu Leu Val Ser Gln Gln Ser Pro Cys
                95                  100                 105

Gly Arg Ala Thr Ser Ser Ser Arg Val Trp Trp Asp Ser Ser Phe
                110                 115                 120

Leu Gly Gly Val Val His Leu Glu Ala Gly Glu Glu Val Val Val
                125                 130                 135

Arg Val Leu Asp Glu Arg Leu Val Arg Leu Arg Asp Gly Thr Arg
                140                 145                 150

```
-continued

Ser Tyr Phe Gly Ala Phe Met Val
                155

<210> SEQ ID NO 10
<211> LENGTH: 7
<212> TYPE: PRT
<213> ORGANISM: Homo sapiens
<220> FEATURE:
<221> NAME/KEY: domain
<222> LOCATION: 112..118
<223> OTHER INFORMATION: THANK terminal sequence

<400> SEQUENCE: 10

Leu Lys Ile Phe Glu Pro Pro
                5

<210> SEQ ID NO 11
<211> LENGTH: 26
<212> TYPE: DNA
<213> ORGANISM: artificial sequence
<220> FEATURE:
<221> NAME/KEY: primer_bind
<223> OTHER INFORMATION: PCR primer used for amplifying the cDNA
      encoding the extracellular domain of THANK

<400> SEQUENCE: 11
gcgggatccc agcctccggg cagagc                                          26

<210> SEQ ID NO 12
<211> LENGTH: 27
<212> TYPE: DNA
<213> ORGANISM: artificial sequence
<220> FEATURE:
<221> NAME/KEY: primer_bind
<223> OTHER INFORMATION: PCR primer used for amplifying the cDNA
      encoding the extracellular domain of THANK

<400> SEQUENCE: 12
gcgtctagat cacagcactt tcaatgc                                         27

<210> SEQ ID NO 13
<211> LENGTH: 5
<212> TYPE: PRT
<213> ORGANISM: Homo sapiens
<220> FEATURE:
<221> NAME/KEY: domain
<222> LOCATION: 134..138
<223> OTHER INFORMATION: THANK terminal sequence

<400> SEQUENCE: 13

Ala Val Gln Gly Pro
                5
```